(12) United States Patent
Susel et al.

(10) Patent No.: US 7,816,915 B2
(45) Date of Patent: Oct. 19, 2010

(54) MINIATURE COILS ON CORE WITH PRINTED CIRCUIT

(75) Inventors: Pesach Susel, Haifa (IL); Shlomo Fried, Zichron Yaakov (IL); Avi Shalgi, Tel Aviv (IL); Dan Raz, Haifa (IL); Dror Benatav, Tel Aviv (IL)

(73) Assignee: Biosense Webster, Inc., Diamond Bar, CA (US)

( * ) Notice: Subject to any disclaimer, the term of this patent is extended or adjusted under 35 U.S.C. 154(b) by 946 days.

(21) Appl. No.: 11/327,058

(22) Filed: Jan. 6, 2006

(65) Prior Publication Data

US 2007/0157828 A1    Jul. 12, 2007

(51) Int. Cl.
G01R 33/02    (2006.01)
H01F 27/30    (2006.01)

(52) U.S. Cl. .................. 324/258; 336/199; 336/208

(58) Field of Classification Search .......... 324/258; 336/65, 199–200, 206, 208, 232; 361/736, 361/760–761
See application file for complete search history.

(56) References Cited

U.S. PATENT DOCUMENTS

| | | | |
|---|---|---|---|
| 4,103,197 A * | 7/1978 | Ikegami et al. ............ 310/267 |
| 5,167,626 A | 12/1992 | Casper et al. | |
| 5,607,329 A * | 3/1997 | Cho et al. ................ 440/6 |
| 6,133,667 A * | 10/2000 | Sawada et al. ......... 310/216.001 |
| 6,161,032 A | 12/2000 | Acker | |
| 6,201,387 B1 | 3/2001 | Govari | |
| 6,239,724 B1 | 5/2001 | Doron et al. | |
| 6,261,247 B1 | 7/2001 | Ishikawa et al. | |
| 6,366,799 B1 | 4/2002 | Acker et al. | |
| 6,617,948 B2 * | 9/2003 | Kuroshima et al. ........... 336/83 |
| 6,690,255 B2 | 2/2004 | Caramela et al. | |
| 6,788,967 B2 | 9/2004 | Ben-Haim et al. | |
| 2003/0120150 A1 | 6/2003 | Govari | |
| 2004/0263285 A1 | 12/2004 | Suzuki et al. | |

FOREIGN PATENT DOCUMENTS

| | | |
|---|---|---|
| EP | 0 262 329 A1 | 4/1988 |
| EP | 1 315 178 B1 | 5/2003 |
| EP | 1 570 782 A2 | 9/2005 |
| JP | 03036707 A * | 2/1991 |
| JP | 2000353867 A * | 12/2000 |
| WO | 99/49783 A1 | 10/1999 |

OTHER PUBLICATIONS

Kondo et al, Translation of JP02000353867A, Dec. 2000.*
Ezaki et al., English Translation of Abtract of JP 03036707 A, Feb. 1991.*

(Continued)

*Primary Examiner*—Bot L LeDynh
(74) *Attorney, Agent, or Firm*—Louis J. Capezzuto

(57) ABSTRACT

A method for producing a coil assembly includes overlaying printed circuit traces on a core. The traces include terminals for coupling to conductive connections on a base on which the coil assembly is to be mounted. Two or more wires are wrapped around the core so as to define two or more coils, wrapped in different, respective directions. The ends of the wires are coupled to the printed circuit traces, so as to connect the wires through the traces to the terminals.

18 Claims, 5 Drawing Sheets

OTHER PUBLICATIONS

Partial English Translation of EP1315178, May 28, 2003.*
Biosense Webster, Inc., U.S. Appl. No. 10/706,298—pending.
Biosense Webster, Inc., U.S. Appl. No. 10/754,751—pending.
Biosense Webster, Inc., U.S. Appl. No. 11/062,258—pending.
Biosense Webster, Inc., U.S. Appl. No. 11/063,094—pending.
EP Search Report EP 07 25 0036 Jul. 7, 2009.

* cited by examiner

MINIATURE COILS ON CORE WITH PRINTED CIRCUIT

FIELD OF THE INVENTION

The present invention relates generally to magnetic field transducers, and specifically to methods for producing miniature, multi-axis coils and devices produced by such methods.

BACKGROUND OF THE INVENTION

Wireless devices commonly include magnetic field transducers in the form of one or more coils wound on a core. Such transducers may be used to sense or extract energy from external magnetic fields, using the current or voltage that is induced in the coils by the fields. Transducers of this sort may alternatively be used as magnetic field generators, by applying a driving current to the coils. One application of such transducers is in wireless position transponders, as described, for example, by Govari in U.S. Patent Application Publication US 2003/0120150 A1, and by Doron et al. in U.S. Pat. No. 6,239,724. The disclosures of both of these publications are incorporated herein by reference.

In some applications, multiple coils may be wound in different directions around the same core, in order to transmit or receive magnetic fields along multiple different axes. For example, PCT patent publication WO 00/38571 A1 and U.S. Pat. No. 6,261,247, to Ishikawa et al., whose disclosures are incorporated herein by reference, describe an anatomical position sensing system using one or more substantially spherical transponders for measuring relative positions and distances. The transponders are capable of receiving and transmitting RF signals, thus communicating between themselves and with a separate CPU. In one embodiment, the transponder is fabricated on a spherical substrate and includes nine coils in three sets of three coils. Each set is orthogonal to the others and comprises three coils: one transmit coil, one receive coil, and one power coupling coil. The coil sets are grouped in this fashion to ensure that at least one coil set is oriented to provide potentially optimum power coupling and signal communication therewith.

Another example of the use of multi-axis magnetic coils in a medical device is described by Casper et al. in U.S. Pat. No. 5,167,626, whose disclosure is also incorporated herein by reference. This patent relates to a medical capsule device actuated by radio-frequency (RF) signal. In one embodiment, three copper wire coils are orthogonally wound around a common ferrite core. The core serves to increase the effective cross-sectional area of the coils. The coil assembly thus provides for the interception of more flux from a magnetic field transmitter and minimizes the dependence of received radio-frequency signal energy on the orientation of the capsule device within the gastrointestinal tract.

There are techniques known in the art for forming or mounting a single-axis magnetic coil on a circuit substrate. For example, U.S. Pat. No. 6,690,255, to Caramela et al., describes a surface-mountable component comprising an elongated core having first and second ends and first and second supports for supporting the core. Each of the supports defines a receptacle for receiving one of the first and second ends of the core. Metallized pads are provided on the supports for electrically connecting and mounting the support to a printed circuit board. At least one wire is wound about a portion of the core and has its ends electrically connected to the metallized pads of the supports. Components of this sort are available from Coilcraft Inc. (Cary, Ill.).

SUMMARY OF THE INVENTION

Embodiments of the present invention provide methods for producing multi-axis coil assemblies that are suited for mounting on a base with conductive connections, such as a printed circuit substrate or a cable connector. Although these methods may be used in producing coils of any size, they are particularly advantageous in manufacturing miniature transponder and power coils that are to be integrated with other circuit elements. Such coils may be used, inter alia, in medical position sensing applications.

In the embodiments described hereinbelow, printed circuit traces are overlaid on a core, which may comprise magnetic or non-magnetic material. The traces comprise terminals for coupling to a base to which the coil assembly is to be mounted. In some embodiments, the traces are printed directly onto the surface of a suitable core material, such as a ceramic or plastic material. In other embodiments, the traces are printed on a flexible printed circuit material, which is then wrapped around the core. At least two coil wires are wrapped around the core in different, respective directions. The ends of the wires are connected to the printed circuit traces overlying the core, which thus electrically couple the wires through the traces to the terminals.

The coil assembly thus produced can be mounted on the base using the same assembly techniques, such as surface-mount soldering or wire bonding, as are used for conventional circuit components. The novel production techniques provided by the present invention enhance the manufacturability and reliability of miniature coil assemblies, as well as the convenience of integrating such coils with other circuit elements.

There is therefore provided, in accordance with an embodiment of the present invention, a method for producing a coil assembly, including:

overlaying printed circuit traces on a core, the traces including terminals for coupling to conductive connections on a base on which the coil assembly is to be mounted;

wrapping two or more wires around the core so as to define two or more coils, wrapped in different, respective directions, the wires having respective ends; and coupling the ends of the wires to the printed circuit traces, so as to connect the wires through the traces to the terminals.

In some embodiments, the method includes mounting the coil assembly on the base, and soldering or wire-bonding the terminals to the conductive connections so as to connect the wires to other circuitry via the base.

In a disclosed embodiment, overlaying the printed circuit traces includes printing the traces onto the core. Typically, the core includes a dielectric material, which is configured as a bobbin to receive the two or more wires, the bobbin including a flange upon which the terminals are printed. The dielectric material may include at least one of a ceramic and a plastic material. Additionally or alternatively, the core includes a magnetic material.

In another embodiment, overlaying the printed circuit traces includes printing the traces on a flexible dielectric substrate, and placing the dielectric substrate over the core before wrapping the two or more wires.

In some embodiments, overlaying the printed circuit traces includes forming printed calibration coils over the core, and the method includes using the printed calibration coils to calibrate a response of the coils defined by wrapping the two or more wires around the core to a magnetic field.

In disclosed embodiments, wrapping the two or more wires includes wrapping three coils around the core in respective, mutually-orthogonal directions.

The base may include an area of a printed circuit substrate or may be a part of a cable connector.

There is also provided, in accordance with an embodiment of the present invention, a coil assembly, including:

a core;

printed circuit traces overlaid on the core, the traces including terminals for coupling to conductive connections on a base on which the coil assembly is to be mounted; and two or more wires wrapped around the core in different, respective directions so as to define two or more coils, the wires having respective ends, which are coupled to the printed circuit traces, so as to connect the wires through the traces to the terminals.

There is additionally provided, in accordance with an embodiment of the present invention, a sensor, including:

a circuit substrate;

a coil assembly, which is mounted on the circuit substrate, and which includes:

a core;

printed circuit traces overlaid on the core, the traces including terminals, which are coupled to the circuit substrate; and two or more wires wrapped around the core in different, respective directions so as to define two or more coils, the wires having respective ends, which are coupled to the printed circuit traces, so as to connect the wires through the traces to the terminals; and a processing circuit, which is coupled to the circuit substrate so as to receive signals produced by the coil assembly in response to a magnetic field, and which is adapted to process the signals so as to generate data with respect to the magnetic field.

In a disclosed embodiment, the data generated by the processing circuit are indicative of a position of the sensor. The circuit substrate, coil assembly and processing circuit may be contained in a housing suitable for insertion into a body of a patient.

There is further provided, in accordance with an embodiment of the present invention, a sensor, including:

a connector containing a base including conductive connections;

a coil assembly, which is mounted on the circuit substrate, and which includes:

a core;

printed circuit traces overlaid on the core, the traces including terminals, which are coupled to the conductive connections of the connector; and two or more wires wrapped around the core in different, respective directions so as to define two or more coils, the wires having respective ends, which are coupled to the printed circuit traces, so as to connect the wires through the traces to the terminals;

a processing circuit, which is adapted to process signals produced by the coil assembly in response to a magnetic field so as to generate data with respect to the magnetic field; and a cable, coupled between the conductive connections of the connector and the processing circuit so as to convey the signals from the coil assembly to the processing circuit.

The present invention will be more fully understood from the following detailed description of the embodiments thereof, taken together with the drawings in which:

DETAILED DESCRIPTION OF EMBODIMENTS

Figure 1:
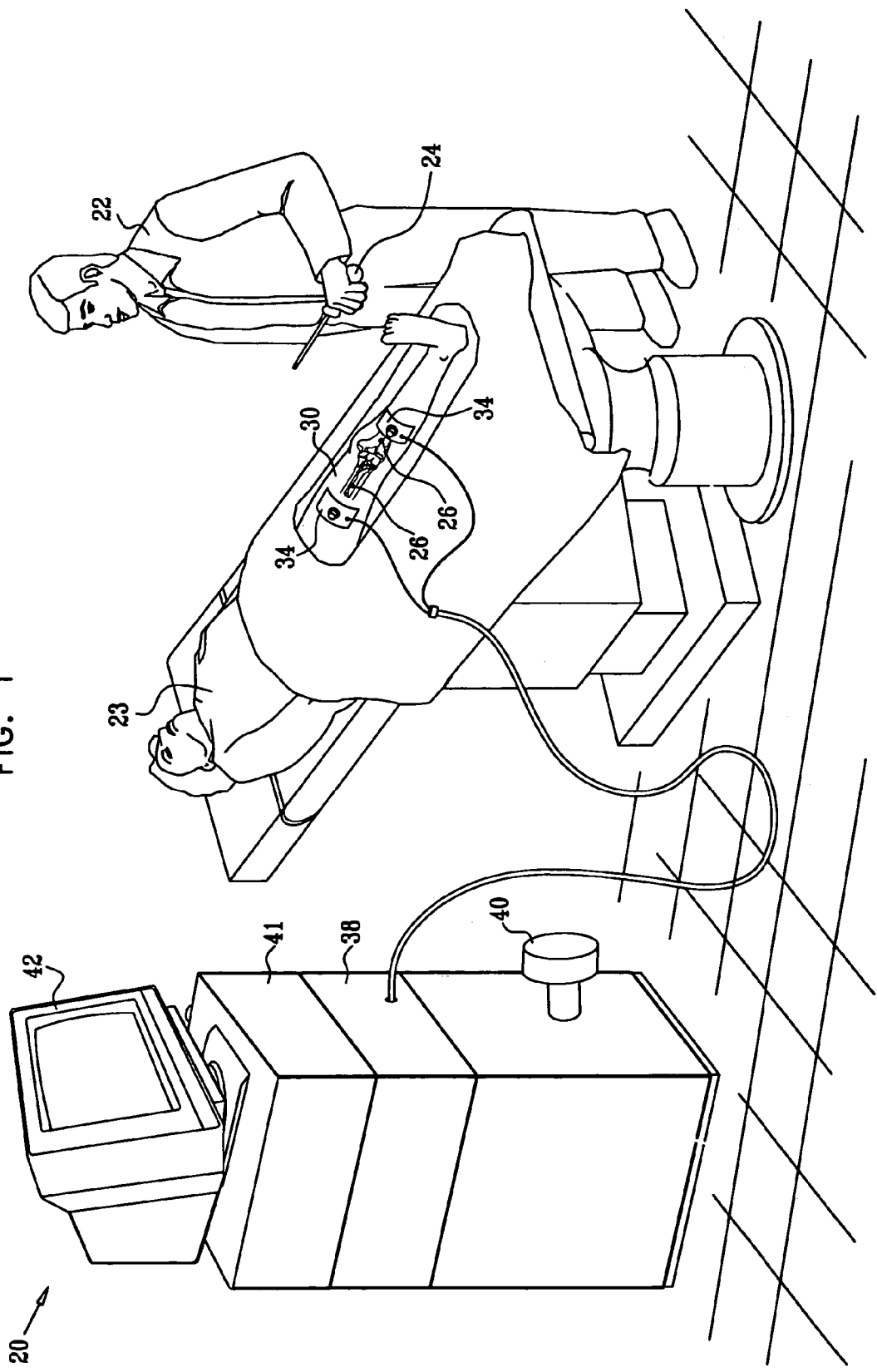
FIG. 1 is a schematic, pictorial illustration showing a magnetic position sensing system used in a medical application, in accordance with an embodiment of the present invention.

FIG. 1 is a schematic, pictorial illustration of a magnetic tracking system 20 used in surgery, in accordance with an embodiment of the present invention. A surgeon 22 performs a medical procedure on a patient 23 using a medical tool 24. Implants 26 are introduced into the patient's body at a surgical site, which is located in this example in a leg 30 of the patient. The tracking system guides the surgeon in performing the procedure, in this example a knee-joint operation, by measuring and presenting the positions of implants 26 and tool 24. The system measures the location and orientation coordinates throughout a working volume that comprises the surgical site.

The coordinates of tool 24 and implants 26 are determined relative to field generators, such as location pads 34, which are fixed to the patient's body. In the example shown in FIG. 1, the pads are placed on the patient's calf and thigh, in proximity to implants 26. A signal generator unit 38 generates drive signals that drive the field generators, typically comprising field generating coils, in location pads 34.

Implants 26 and tool 24 contain miniature, wireless sensor units, which are described in detail hereinbelow. Each sensor unit comprises a position sensor that is designed to sense the magnetic field in its vicinity. The magnetic fields generated by location pads 34 induce currents in the position sensors of the sensor units fitted into tool 24 and implants 26. In response to the induced currents (or corresponding voltages), signal processing and transmitter circuits in each sensor unit generate and transmit position signals that are indicative of the location and orientation of the implant or tool. It is clear that in this context, the position sensors must be very compact and function with high reliability.

The position signals are received by a wireless control unit 40, which is coupled to a computer 41. The computer processes the received signals in order to calculate the relative location and orientation coordinates of tool 24 and implants 26. The results are typically presented to the surgeon on a display 42.

Further details regarding position tracking systems of the sort shown in FIG. 1 can be found in U.S. patent application Ser. No. 11/063,094, filed Feb. 22, 2005, and in U.S. patent application Ser. No. 11/062,258, filed Feb. 18, 2005. These applications are assigned to the assignee of the present patent application, and their disclosures are incorporated herein by reference. Alternatively, the principles of the present invention may be implemented in position tracking systems of other sorts, such as those noted in the Background of the Invention, as well as in other applications of magnetic field transmission and reception, as are known in the art.

Figure 2:
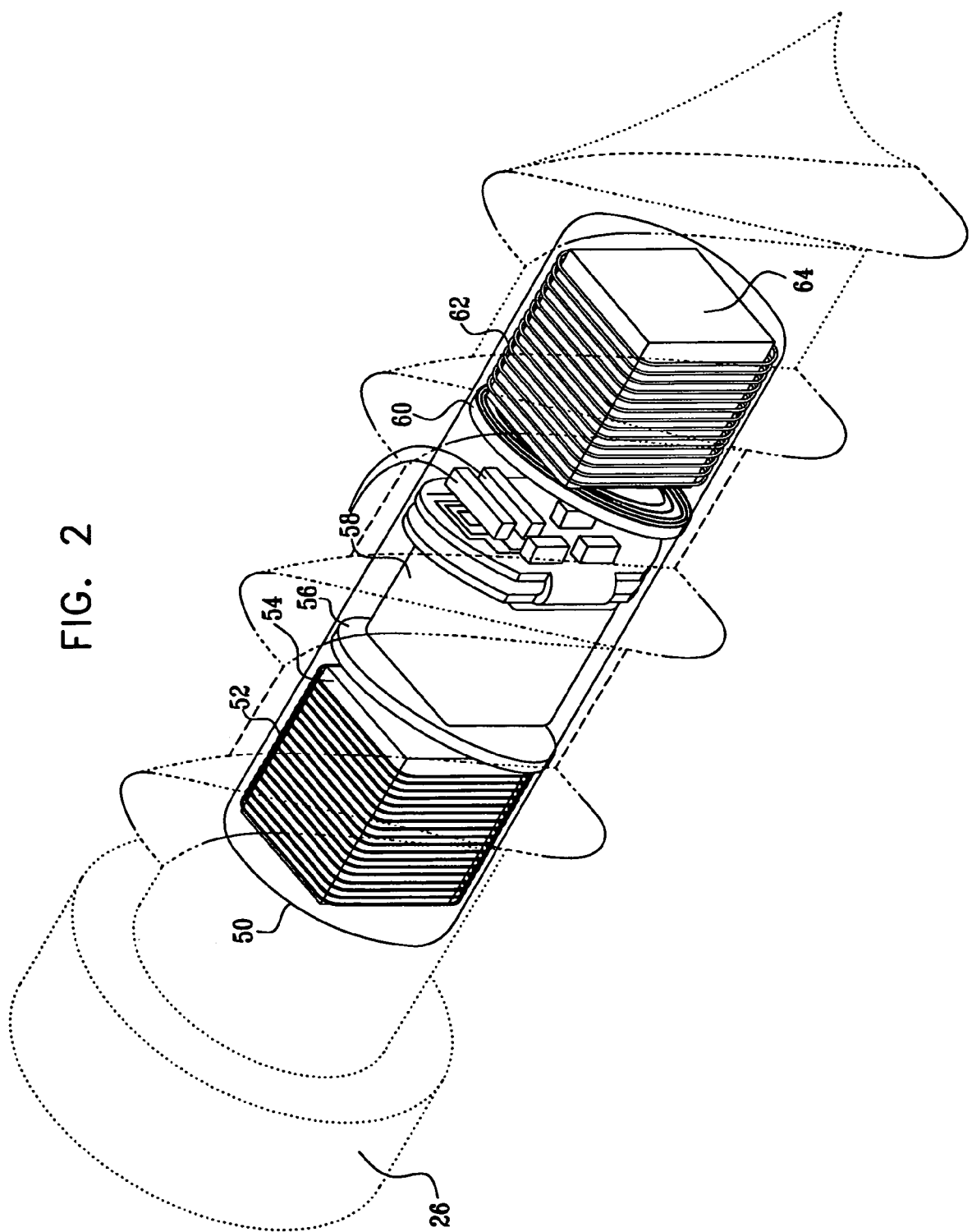
FIG. 2 is a schematic, pictorial illustration showing a magnetic position transponder inside a bone implant, in accordance with an embodiment of the present invention.

FIG. 2 is a schematic, pictorial illustration of a position sensor 50 that is contained in implant 26, in accordance with an embodiment of the present invention. Alternatively, sensor 50 may be contained in or otherwise attached to other types of implants and invasive devices. Sensor 50 in this exemplary embodiment comprises a sensor coil assembly 52, which comprises coil wires wound on a sensor core 54. The core may comprise magnetic or non-magnetic material. Sensor 50 further comprises a power coil assembly 62, and a wireless communication coil 60. The coils are mounted on a suitable substrate 56, such as a flexible printed circuit board (PCB) and are coupled to electronic processing circuitry 58, which is likewise mounted on the substrate. Circuitry 58 receives and processes electrical signals generated by sensor coil assembly 52 in response to the magnetic field generated by location pad 34. Based on these signals, circuitry 58 transmits position data to control unit 40. Further details of the construction and operation of circuitry 58 are described in the above-mentioned U.S. Patent Application Publication US 2003/0120150 A1 and in U.S. patent application Ser. No. 10/706,298, which is assigned to the assignee of the present patent application, and whose disclosure is incorporated herein by reference.

Figure 5:
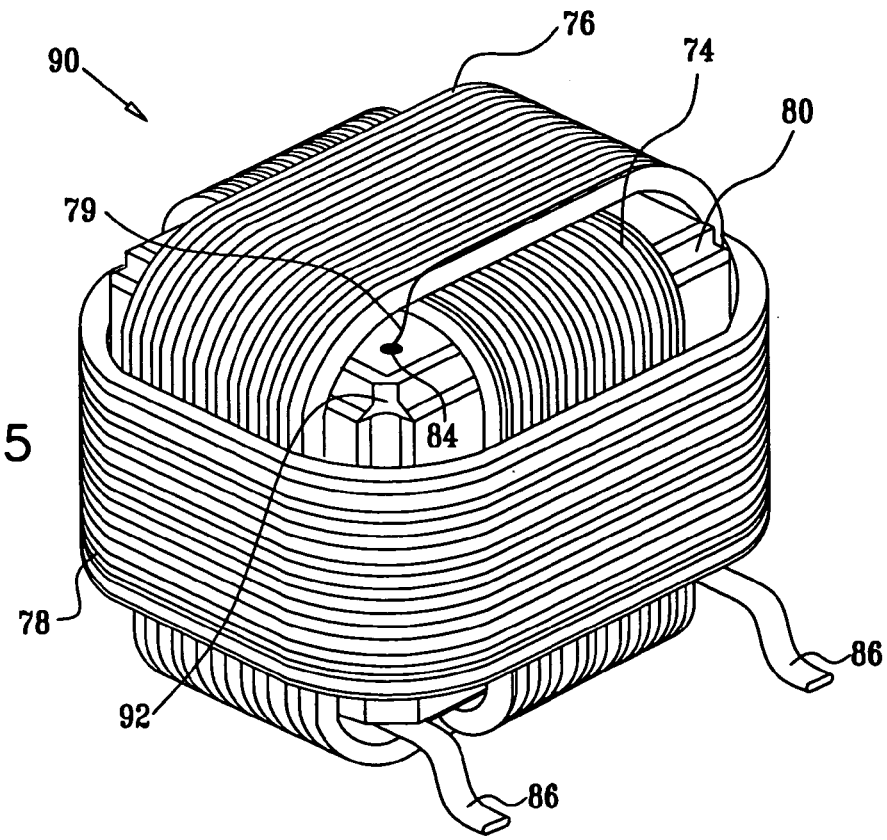
FIG. 5 is a schematic, pictorial illustration showing a coil assembly using the flexible printed circuit of FIG. 4, in accordance with an embodiment of the present invention.

Although for simplicity, FIG. 2 shows only a single coil in each of sensor and power coil assemblies 52 and 62, in practice each assembly typically comprises multiple coils, such as three sensor coils and three power coils. (Multiple sensor coils wound on a common core are shown in FIGS. 3B and 5 below.) The sensor coils are wound together, in mutually-orthogonal directions, on core 54, while the power coils are wound together, in mutually-orthogonal directions, on another core 64. Alternatively, the sensor and power coils may be overlapped on the same core, as described, for example in U.S. patent application Ser. No. 10/754,751, filed Jan. 9, 2004, whose disclosure is incorporated herein by reference.

Figure 3A:
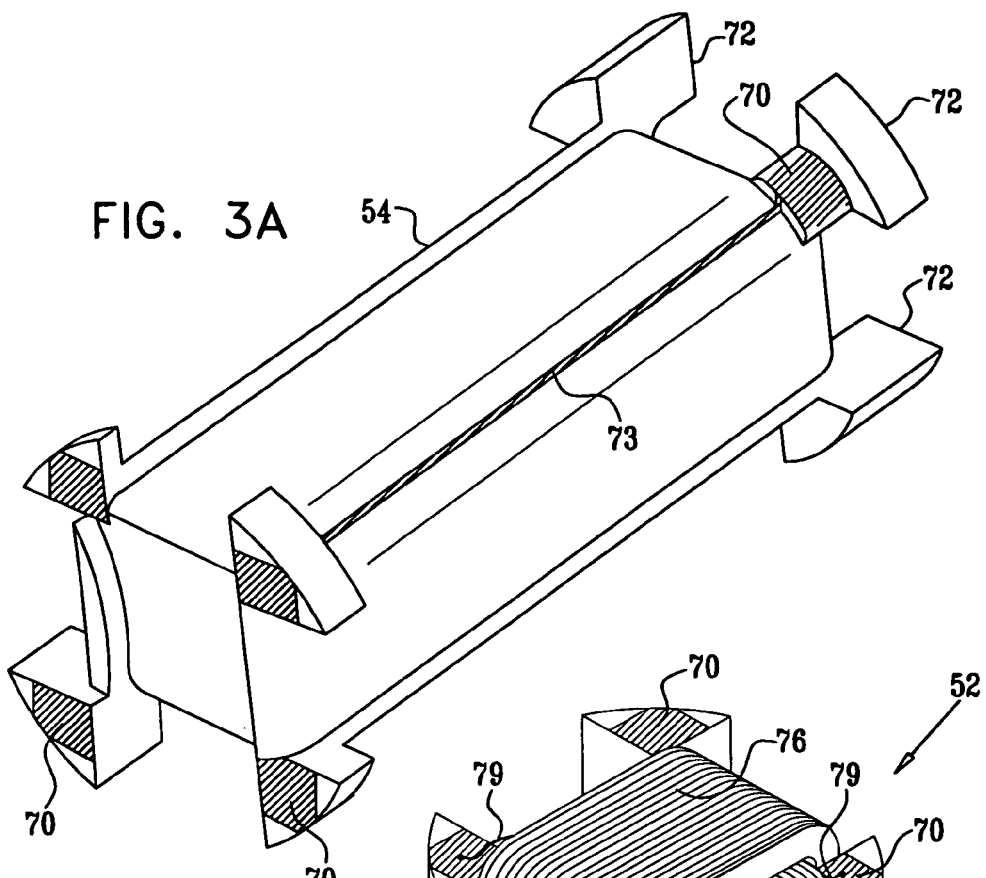
FIG. 3A is a schematic, pictorial illustration showing a core on which circuit traces are printed, in accordance with an embodiment of the present invention.
Figure 3B:
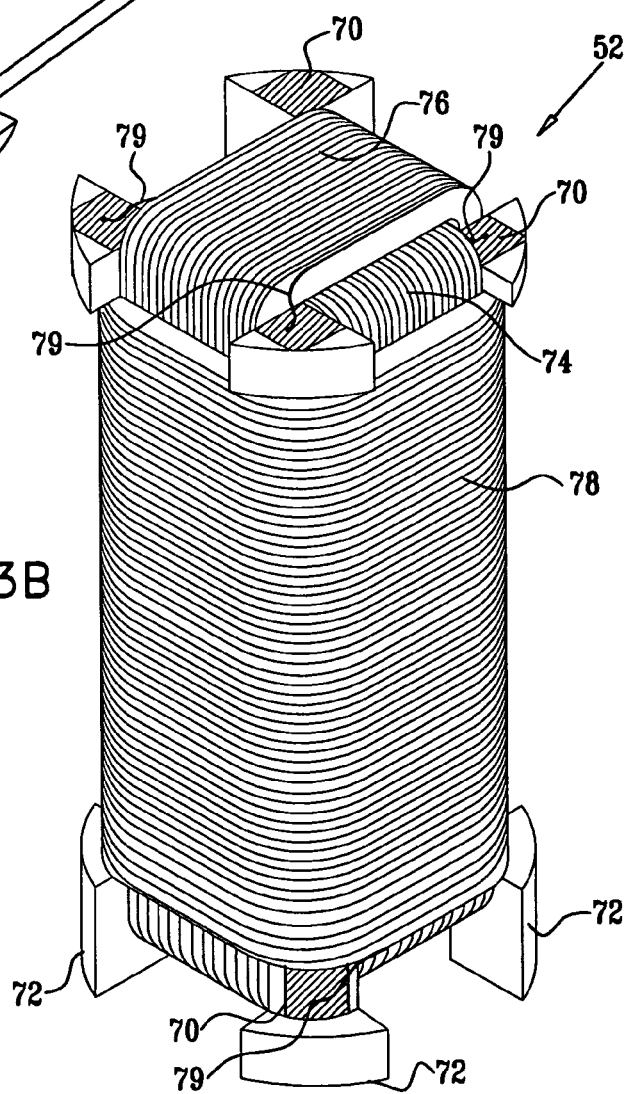
FIG. 3B is a schematic, pictorial illustration showing a coil assembly wound on the core of FIG. 3A, in accordance with an embodiment of the present invention.

FIG. 3A is a schematic, pictorial illustration of core 54, in accordance with an embodiment of the present invention. Core 54 typically comprises a dielectric material, such as a suitable ceramic or plastic material, such as polyetheretherketone (PEEK), which is manufactured in the form of a bobbin, with typical dimensions of about 2×2×5 mm. Optionally, a magnetic ceramic material may be used. Metal terminal pads 70 are printed onto the sides and flanges 72 of the bobbin, using a photolithographic process, for example. The terminal pads printed onto the base of the core, at the outer side of flanges 72, allow the core itself to be mounted and soldered onto a printed circuit board, such as substrate 56, using surface mount manufacturing techniques. Printed circuit traces 73 connect the terminal pads on the sides of the core to the terminal pads on the outer surfaces of the bobbins.

FIG. 3B is a schematic, pictorial illustration showing sensor coil assembly 52, in accordance with an embodiment of the present invention. In this embodiment, three separate coils 74, 76, 78 of thin wire have been wound on core 54 (hidden in this figure). Each of the coils is wrapped around a different, orthogonal axis. The size of the wire and number of turns depends on application requirements, for example, more turns of thinner wire for sensor coil assembly 52, fewer turns of thicker wire for power coil assembly 62. In different implementations, the inventors have used wires of diameter between 10 and 70 μm, with between 40 and 3000 turns of wire around the core. Other implementations will be apparent to those skilled in the art.

To produce assembly 52, core 54 is mounted so as to rotate about the axis of coil 74, and a suitable wire is fastened to the core. The core is then rotated about the axis, and the wire is fed out from a spool until the proper number of turns have been wound on the core. The core is then shifted to rotate about the axis of coil 76, and the core is then rotated so as to wind coil 76 over coil 74. Optionally, a dielectric separator (not shown in the figures) is placed over coil 74 before winding coil 76, in order to reduce parasitic coupling between the two coils. Finally, coil 78 is wound over coil 76 in the same manner. Wire ends 79 of each of the coils are then soldered to appropriate points on terminal pads 70, thus electrically coupling the coil wires to pads on the bottom of flanges 72. Assembly 52 can now be mounted on a printed circuit substrate, such as substrate 56, in the orientation shown in FIG. 3B.

Figure 4:
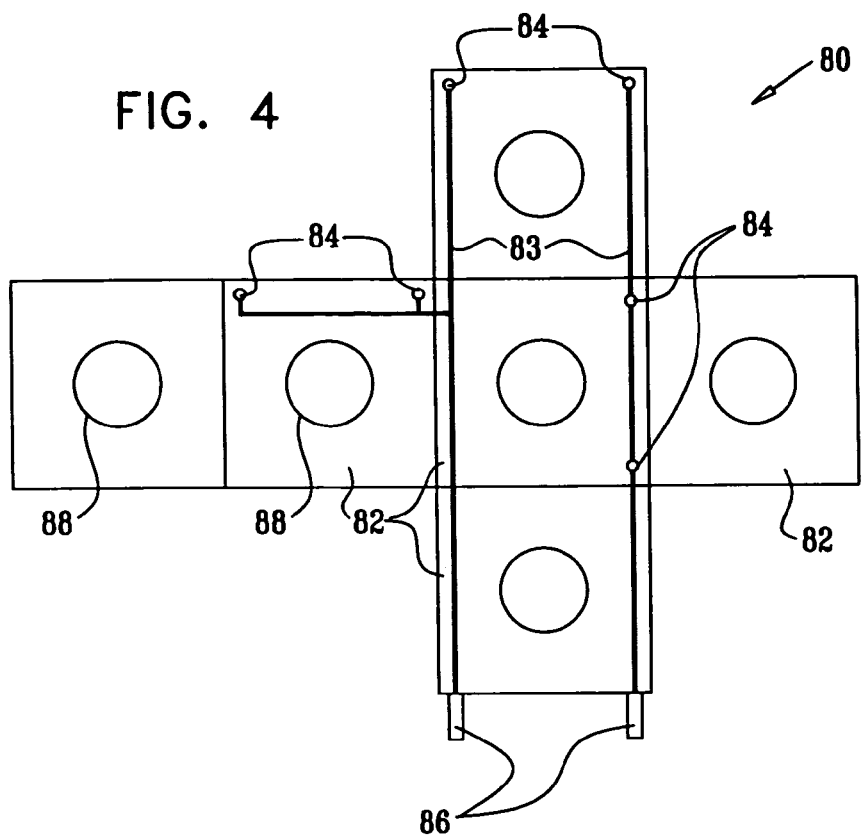
FIG. 4 is a schematic, frontal view of a flexible printed circuit, in accordance with an embodiment of the present invention.

FIG. 4 is a schematic, frontal view of a flexible printed circuit 80, in accordance with an embodiment of the present invention. The flexible printed circuit may be wrapped around a core, as shown below in FIG. 5, when it is not possible or desirable to print circuit traces directly on the core, as in the preceding embodiment. Circuit 80 comprises a thin, flexible dielectric substrate material 82, such as Mylar®, on which conductive traces 83 are printed. Two terminals 84 are also provided in circuit 80 for each of the X-, Y- and Z-coils that will be wrapped on the core. Terminals 84 are coupled by traces 83 to contacts 86, which protrude at the edge of substrate 82.

FIG. 5 is a schematic, pictorial illustration of a coil assembly 90, based on printed circuit 80, in accordance with an embodiment of the present invention. To produce assembly 90, printed circuit 80 is wrapped around a core 92, such as a ferrite, and fastened in place, using a suitable glue, for example. The six segments of the printed circuit are sized to match the faces of the core. Although core 92 is shown in FIG. 5 to have a cubic shape, other core shapes may likewise be used, with appropriate adjustment to the shape and size of printed circuit 80. Each of coils 74, 76 and 78 is then wound on core 92 in the manner described above with regard to coil assembly 52: end 79 of the coil wire is inserted into one of terminals 84, and the core is then rotated to wrap the wire around the core in the proper direction. After completing the winding, the other end of the coil wire is inserted into the other terminal.

When flexible printed circuit 80 has been wrapped around core 92, and the coils have been wound over the printed circuit, contacts 86 remain accessible. These contacts may be soldered to a circuit substrate directly or connected by bonding wires. Thus, coil assembly 60 can be mounted on a substrate, such as substrate 56, along with other electronic components of the sensor, using surface mounting techniques if desired.

In magnetic sensing applications, deviations in the geometry of coils 75, 76, 78 can cause variations in the responses of the coils to an applied magnetic field and thus compromise the accuracy of the sensor. To address this problem, calibration coils 88 may optionally be printed as traces on flexible printed circuit 80, typically on the inner surface (i.e., on the side facing toward core 92, away from coils 74, 76, 78). These calibration coils are likewise connected by traces (not shown) to contacts 86, and may thus be coupled to circuitry on substrate 56. Since these printed calibration coils have a precisely-known geometry, they can be used to calibrate the response of the wire-wound coils, in order to compensate for manufacturing variability in the wire-wound coils. For example, the response of the printed calibration coils to an external magnetic field can be used as a calibration benchmark for the wire-wound coils or, alternatively, the response of the wire-wound coils to a magnetic field generated by driving the printed calibration coils can be measured for calibration purposes.

Figure 6:
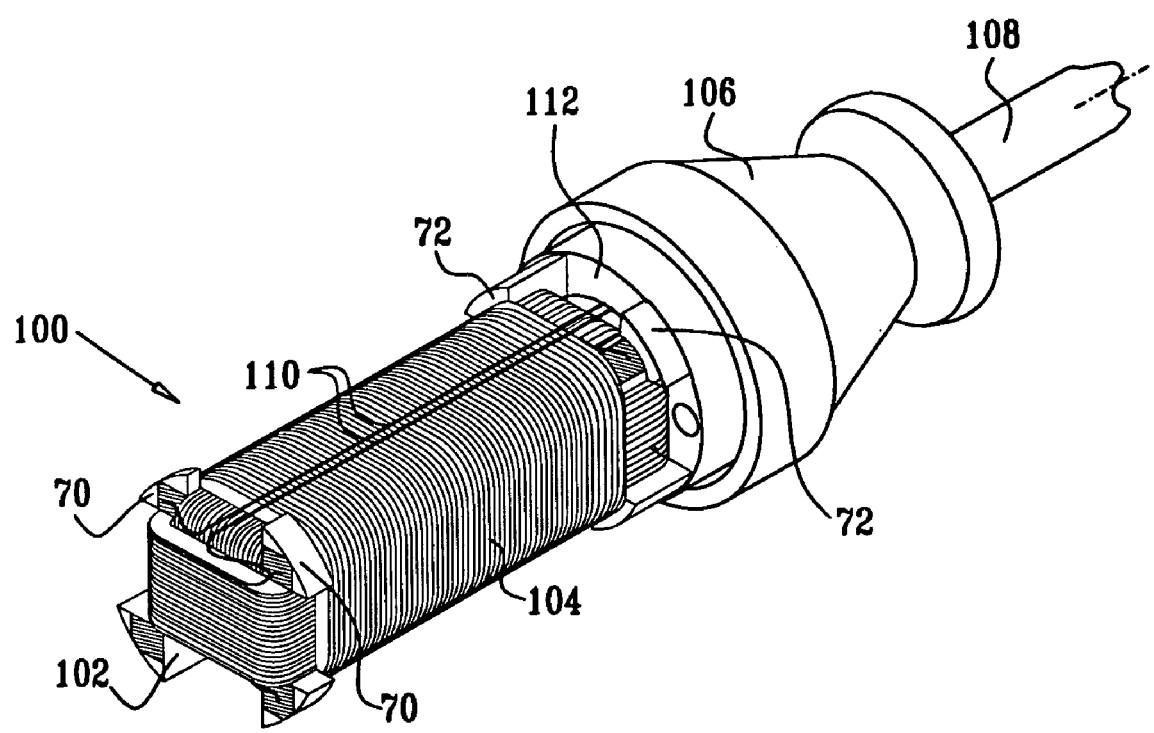
FIG. 6 is a schematic, pictorial illustration showing a coil and cable assembly, in accordance with another embodiment of the present invention.

FIG. 6 is a schematic, pictorial illustration showing a coil assembly 100, which is designed to mate with a connector 106, in accordance with another embodiment of the present invention. Assembly 100 is similar in design and method of manufacture to assembly 52 (FIG. 3B), and comprises a core 102 with coils 104 wound thereon. The wire ends of the coils are then soldered to appropriate points on terminal pads 70, as described above.

In the present embodiment, however, flanges 72 of coil assembly 100 are mounted on a base 112 in connector 106, which couples the coil assembly to a multi-conductor cable 108. Base 112 may comprise conductive contacts that engage the terminals on flanges 72. Additionally or alternatively, conductors 110 of cable 108 may extend out of connector 106 and connect, typically by wire bonding or another suitable technique, to pads 70. When assembly 100 comprises three coils 104, for example, all six ends of the coil wires may be connected easily and reliably to respective conductors of cable 108 using one or both of these techniques.

After connecting coil assembly 100 to connector 106, the coil assembly (and possibly the connector, as well) may be encapsulated in a sealed, biocompatible housing, and may then be inserted into the body of a patient, as described above. Cable 108 conveys the signals from the coil assembly to processing circuitry outside the body, which processes the signals to determine position coordinates of the coil assembly as described above. This arrangement, in which the coil alone is contained in the sensor unit that is inserted into the patient's body and is connected to the processing circuitry by cable 108, is useful in minimizing the size of the sensor unit and avoiding problems that may be associated with wireless power and data transmission to and from the sensor.

Although the embodiments described above relate particularly to construction of magnetic field sensors in a position tracking application, the novel techniques described above for overlaying conductive traces on a core and connecting coil wires to such traces may be used, mutatis mutandis, in other applications and configurations. For example, multi-axis coil components may be made in this way for purposes of generating and transmitting magnetic fields. Furthermore, the conductive traces that are overlaid on the core of an inductive coil in accordance with the techniques described above may also be used for integrating circuitry of other types with the coil in a single, self-contained unit.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for producing a coil assembly, comprising:
   overlaying printed circuit traces on a core by printing the circuit traces onto the core, the traces comprising terminals for coupling to conductive connections on a base on which the coil assembly is to be mounted;
   wrapping two or more wires around the core and printed circuit traces so as to define two or more coils, wrapped in different, respective directions, the wires having respective ends; and
   coupling the ends of the wires to the printed circuit traces, so as to connect the wires through the traces to the terminals.

2. The method according to claim 1, and comprising mounting the coil assembly on the base, and soldering the terminals to the conductive connections so as to connect the wires to other circuitry via the base.

3. The method according to claim 1, and comprising mounting the coil assembly on the base, and wire-bonding the terminals to the conductive connections so as to connect the wires to other circuitry via the base.

4. The method according to claim 1, wherein the core comprises a dielectric material, which is configured as a bobbin to receive the two or more wires, the bobbin comprising a flange upon which the terminals are printed.

5. The method according to claim 4, wherein the dielectric material comprises at least one of a ceramic and a plastic material.

6. The method according to claim 1, wherein the core comprises a magnetic material.

7. A method for producing a coil assembly, comprising:
   overlaying printed circuit traces on a core, the traces comprising terminals for coupling to conductive connections on a base on which the coil assembly is to be mounted;
   wrapping two or more wires around the core and printed circuit traces so as to define two or more coils, wrapped in different, respective directions, the wires having respective ends; and
   coupling the ends of the wires to the printed circuit traces, so as to connect the wires through the traces to the terminals,
   wherein overlaying the printed circuit traces comprises forming printed calibration coils over the core, and comprising using the printed calibration coils to calibrate a response of the coils defined by wrapping the two or more wires around the core to a magnetic field.

8. The method according to claim 1, wherein wrapping the two or more wires comprises wrapping three coils around the core in respective, mutually-orthogonal directions.

9. The method according to claim 1, wherein the base comprises an area of a printed circuit substrate.

10. The method according to claim 1, wherein the base is a part of a cable connector.

11. A coil assembly, comprising:
    a core;
    printed circuit traces overlaid on the core, the circuit traces printed onto the core, the traces comprising terminals for coupling to conductive connections on a base on which the coil assembly is to be mounted; and
    two or more wires wrapped around the core and printed circuit traces in different, respective directions so as to define two or more coils, the wires having respective ends, which are coupled to the printed circuit traces, so as to connect the wires through the traces to the terminals.

12. The assembly according to claim 11, wherein the core comprises a dielectric material, which is configured as a bobbin to receive the two or more wires, the bobbin comprising a flange upon which the terminals are printed.

13. The assembly according to claim 12, wherein the dielectric material comprises at least one of a ceramic and a plastic material.

14. The assembly according to claim 11, wherein the core comprises a magnetic material.

15. The assembly according to claim 11, wherein the printed circuit traces comprise printed calibration coils, which are used to calibrate a response of the coils defined by wrapping the two or more wires around the core to a magnetic field.

16. The assembly according to claim 11, wherein the two or more wires are wrapped around the core so as to define three coils, which are wrapped in respective, mutually-orthogonal directions.

17. The assembly according to claim 11, wherein the base comprises an area of a printed circuit substrate.

18. The method according to claim 11, wherein the base is a part of a cable connector.

* * * * *